United States Patent

Rubino

[11] Patent Number: 5,856,491
[45] Date of Patent: Jan. 5, 1999

[54] METHOD OF MAKING TERITIARY HINDERED AMINES

[75] Inventor: Mark R. Rubino, Pittsburgh, Pa.

[73] Assignee: Aristech Chemical Corp., Pittsburgh, Pa.

[21] Appl. No.: 906,788

[22] Filed: Aug. 9, 1997

[51] Int. Cl.$^6$ ............... C07D 211/00; C07D 211/30; C07D 211/08; C07D 211/36
[52] U.S. Cl. ............. 546/184; 546/189; 546/190; 546/191; 546/192; 546/218; 546/222; 546/242
[58] Field of Search ................... 546/189, 242, 546/184, 190, 191, 192, 218, 222

[56] References Cited

U.S. PATENT DOCUMENTS

| | | | |
|---|---|---|---|
| 3,940,363 | 2/1976 | Murayama et al. | 260/45.8 N |
| 3,956,310 | 5/1976 | Chalmers | 260/309.7 |
| 3,974,127 | 8/1976 | Tanikella et al. | 260/75 |
| 3,975,357 | 8/1976 | Murayama et al. | 260/45.8 N |
| 4,014,887 | 3/1977 | Randell et al. | 260/293.8 |
| 4,731,448 | 3/1988 | Issler et al. | 546/248 |

OTHER PUBLICATIONS

Robertson, Biel and DiPierro, "2,2,6,6–Tetramethylpiperidines and Related Compounds", J.Org Chem 6, 381, (1963).

Shen, Su, Li, Zhu, and Su, "Alkylation of tetramethylpiperidinol", Chem Abst. 108:221569t.

Sosnovsky and Konieczny, "Utilization of the Sterically Hindered Base, 4–Hydroxy–2,2,6,6–tetramethylpiperidine, as a Hydrogen Halide Acceptor", Z. Naturforsch 33b, 792–796 (1978).

Karrer, Friedrich E., "Tetra– and Pentaalkylpiperidin–Derivate von Polyacryl– und Polymethacrylestern, Polyacryl– und Polymethacrylamiden", Macromol. Chem. 818,595–633 (1980).

Kurumada, Ohsawa, Fujita, and Toda, "Effect of N–Substituents of Hindered Amine on Photo–Oxidation of Polypropylene", J. Polymer Science, Polymer Chem Edition 22, 277–281 (1984).

Bonnesen, Puckett, Honeychuck and Hersh, "Catalysis of Diels–Alder Reactions vy Low Oxidation State Transition–Metal Lewis Acids", J, Am. Chem. Soc. 111 6070 (1989).

Kurumada, Ohsawa, Oda, Fujita, Toda, and Yoshioka, "Photostabilizing Activity of Tertiary Hindered Amines", J. Polymer Science, Polymer Chem Ed 23 1477 (1985).

Dagonneau, Kagan, Mikhailov, Rozantsev, and Sholle, "Chemistry of Hinderdd Amines from the Piperidine Series", Synthesis 1984 895.

Hall, Jr. "Steric Effects on the Base Strengths of Cyclic Amines", J. Am. Chem. Soc. 79 5444 (1957).

Anderson, Casarini, Corrie and Lunazzi, "The Measurement of the One–Fold Rotational Barrier of Eclipsed Bonds: A Dynamic . . . " J Am Chem Soc., Perkins Trans. 2 1993, 1299.

*Primary Examiner*—John Kight
*Assistant Examiner*—Raymond Covington
*Attorney, Agent, or Firm*—William L. Krayer

[57] ABSTRACT

Fully hindered secondary amines, typically tetramethyl piperidine, are reacted with terminally unsaturated electrophilic compounds having at least five carbon atoms to obtain tertiary hindered amines. The reaction is conducted with an excess of secondary amine, preferably in the presence of a specified solvent such as N-methyl pyrrolidinone.

24 Claims, No Drawings

METHOD OF TERITIARY HINDERED AMINES

TECHNICAL FIELD

This invention relates to a method of making polymerizable tertiary hindered amines beginning with certain secondary hindered amines as reactants. The invention involves reaction of the secondary hindered amine with an appropriate terminally unsaturated hydrocarbon electrophile in the presence of a solvent selected from N,N-dialkylamides and N,N,N'N'-tetraalkylureas. The alkyl groups in the solvent may form a ring as in N-methylpyrrolidinone.

BACKGROUND OF THE INVENTION

Hindered amines are widely used as stabilizers for polyolefins. The largest category of hindered amine stabilizers is made from triacetoneamine, a hindered secondary amine. In some stabilizers sold commercially, the hindered amine remains secondary, unchanged from the parent triacetoneamine. In other commercial stabilizers the hindered amine is tertiary, and alkylation of the hindered secondary amine is required during their production.

The alkylation of hindered secondary amines has a general drawback: many hydrocarbon electrophiles eliminate to alkenes in competition with amine alkylation. Elimination converts the electrophile into a waste alkene, and it makes the secondary amine into an ammonium salt. The ammonium salt does not alkylate without being turned back into a free amine.

Due to elimination, numerous hindered tertiary amines which might exist are presumed to be costly and probably impractical, based on prior art. In commercial stabilizers, only electrophiles which cannot easily eliminate are used to alkylate hindered secondary amines. Thus, the available hindered tertiary amines contain either 2-hydroxyethyl groups from alkylation by ethylene oxide, or they contain methyl groups from alkylation by methyl electrophiles. Methyl groups may also be introduced by reductive alkylation with formaldehyde, a reaction which is not readily extended to alkyl groups other than methyl.

For example, alkylation by ethylene oxide is described in U.S. Pat. No. 4,731,448 issued Mar. 15, 1988 to Ciba-Geigy. The alkylation of 2,2,6,6-tetramethylpiperidine (TMP) by ethylene oxide is described in J. Org. Chem. 6 381 (1963).

An example of the methylation with formaldehyde may be seen in column 5 of U.S. Pat. No. 3,974,127 of Aug. 10, 1976 to Du Pont.

The difficult alkylation of hindered secondary amines can lead to side reactions other than elimination. In Chem. Abstr. 108:221569t Huaxue Shiji 9, 212 (1987) authors D. Shen, B. Su, Z. Yliang L. Shu and X. Su describe competing oxygen alkylation during the attempted N-alkylation of 2,2,6,6-tetramethylpiperidin-4-ol (TMPOH).

Elimination can be prominent during efforts to alkylate hindered secondary amines. Note that TMPOH has been used as a reagent in a method for alkyl bromide dehydrobromination. In Z. Naturforsch, 33b, 792–796 (1978), Konieczny and Sosnovsky heat 1-bromoheptane and 1-bromooctane in dimethyl sulfoxide with TMPOH. Heptene and octene are isolated in yields of 82% and 93%, respectively. Also obtained in each case is a high yield of the hydrobromide salt of TMPOH.

A method of alkylating TMPOH is disclosed in U.S. Pat. No. 4,014,887 of Mar. 29, 1977 to Ciba-Geigy. In example 1, 12.5 parts 1-bromododecane and 15.7 parts TMPOH are heated to reflux in 50 parts ethyl alcohol for 72 hours. No yield is given for the claimed product 1-(1-dodecyl)-2,2,6,6,-tetramethylpiperidin-4-ol. The only analytical data provided are combustion analysis and melting point, and these do not prove the absence of the ether 4-(1-dodecyloxy)-2,2,6,6-tetramethylpiperidine. In addition to uncertain product purity, this method may suffer from a low yield. The three day reaction time is highly undesirable.

Three days at reflux are also used in U.S. Pat. No. 3,956,310 (May 11, 1976 to Ciba-Geigy). In example 25, a large molar excess of bromohexane is heated in acetonitrile with TMPOH. The isolated yield is only 27% of the theoretical for 1-(1-hexyl)-2,2,6,6-tetramethylpiperidin-4-ol, based on TMPOH.

U.S. Pat. No. 4,014,887 was filed in the United Kingdom as no. 48601 in 1972. According to Chem. Abstr. 81:153691, UK 48601/72 is also DE 2,352,658 on Apr. 25, 1974. In Makromol. Chem. 818, 595–633 (1980), F. E. Karrer cites DE 2,352,658 as reference 58. Karrer reports the formation of 1-(1-butyl)-2,2,6,6-tetramethylpiperidin-4-ol in 69% yield using the method of reference 58. Since Karrer characterizes the product only by melting point, the absence of the ether 4-(1-butoxy)-2,2,6,6-tetramethylpiperidine is not proven.

Authors Kurumada, Ohsawa, Fujita and Toda in J. of Polymer Science: Polymer Chem. Edition, 22, 277 (1984) alkylate 4-benzoyloxy-2,2,6,6-tetramethylpiperidine (6.6 parts) with n-butyl iodide (25 parts) in N,N-dimethylformamide (47 parts) in the presence of potassium carbonate (6 parts). The reaction temperature is 130°–140° C. for 29 hours. The large molar excess of butyl iodide is an inefficient use of this electrophile, and might lead to acidification of the reaction mixture through elimination to butene and hydrogen iodide. The hydrogen iodide will form ammonium salt of the starting material which will not alkylate, reducing conversion and yield. The combination of hydrogen iodide and potassium carbonate at elevated temperature might hydrolyze the benzoate ester for a loss of yield and purity. The potassium carbonate at elevated temperature might decompose the butyl iodide. These drawbacks lead to a low yield of 44%.

In U.S. Pat. No. 3,940,363 (Feb. 24, 1976 to Sankyo) the bisalkylation of 4-benzoyloxy-2,2,6,6-tetramethylpiperidine is described. The yield of diamine product is unspecified using either 1,2-dibromoethane at reflux for four hours, or using 1,6-dibromohexane at reflux. The use of 5 parts 1,2-dibromoethane to 3 parts 4-benzoyloxy-2,2,6,6-tetramethylpiperidine is a large molar excess of alkyl bromide, so the reaction mixture might become acidic by elimination of hydrogen bromide. An acidic reaction mixture could decompose a terminal alkene electrophile.

One object of this invention is the preparation of N-alkylated derivatives of TMPOH free of O-alkylated (ether) impurities and in an overall high state of purity. Furthermore, this invention achieves shorter reaction time. The yield with respect to electrophiles is improved for those electrophiles prone to elimination.

An alkylation of 2,2,6,6,-tetramethylpiperidine (TMP) is described in U.S. Pat. No. 3,975,357 (Aug. 17, 1976 to Sankyo in referential example 1. Over 120 hours at 125°–130° C., 56.4 parts TMP and 38.6 parts 1-bromooctane give 1-(1-octyl)-2,2,6,6-tetramethylpiperidine in unspecified yield. The five day reaction time is highly undesirable. The same method is described using 1-bromododecane, also with no yield.

The long reaction times used in the prior art during hindered amine alkylation do not minimize the risk of terminal to internal alkene isomerization. Terminal alkenes are less stable than their internal isomers. In addition, the long reaction times cause inefficient preparation.

A published synthesis of 1-(1-butyl)-2,2,6,6-tetramethylpiperidine requires 37 hours at 50° C. In J. Am. Chem. Soc. 111 6070 (1989) Bonessen, Puckett, Honeychuck and Hersh obtain 3.5 parts product (64% yield based on TMP) from 3.9 parts TMP and 26.9 parts 1-iodobutane. Also present during the reaction are 5.5 parts potassium carbonate and 28.3 parts N,N-dimethylformamide. The large excess of electrophile used would be uneconomical on a practical scale, particularly so with any expensive electrophile bearing a terminal alkene. The presence of the added carbonate base allows higher than 50% TMP conversion, but it precludes the higher reaction temperatures used in the present invention; the carbonate would decompose the electrophile as temperatures are increased. Because of the excess of iodobutane the reaction mixture could become acidic; an acidic reaction mixture would decompose a terminal alkene.

A synthesis of 1-ethyl-2,2,6,6-tetraethylpiperidine requires ten hours at 50° C. In J. Polymer Sci: Polymer Chem. Ed. 23 1477 (1985), Kurumada et al obtain 6.8 parts product from 14.1 parts TMP (40% yield based on TMP) using 30 parts ethyl iodide and 8 parts potassium carbonate in 14 parts N,N-dimethylformamide. This method uses excess iodoethane, requires added carbonate, and gives a low yield.

Authors Dagonneau, Kagan, Mikhailov, Rozantsev and Sholle in Synthesis 1984 895 review hindered amines and cite Hall, J. Am. Chem Soc. 79 5444 (1957) for alkylations of TMP with methyl toluenesulfonate and ethyl toluenesulfonate. The 63% methylation yield in 30 minutes at 100° C. drops to a 9% yield of 1-ethyl-2,2,6,6-tetramethylpiperidine using prolonged heating.

The difficulty in making tertiary amines from hindered secondary amines is shown by a synthesis of 1-(1-propyl)-2,2,6,6,-tetramethylpiperidine as described by Anderson, Casarini, Corrie and Lunazzi in J. Chem. Soc., Perkin Trans. 2 1993, 1299. TMP (7.5 parts) is combined with excess propionyl chloride and triethylamine to give 5.3 parts crude amide. Reduction by 1.5 parts lithium aluminum hydride gives only 1.3 parts product, for a yield of 13%. In addition to the multiple steps and the low yield, the metal hydride reagent is impractical.

SUMMARY OF THE INVENTION

In the present invention, certain hindered secondary heterocyclic amines are converted to hindered tertiary amines by reaction with primary carbon electrophiles at temperatures above 100° C. in the presence of amide or urea solvents. The hindered tertiary amines are useful as heat and light stabilizers in synthetic resins, or as stabilizer precursors.

The starting materials are heterocyclic amines of the formula

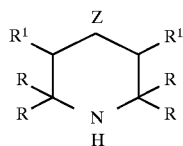

where each R is independently an alkyl group having from one to two carbon atoms, each $R^1$ is H or $CH_3$, Z is a non-nucleophilic group; preferably Z is H, an alkyl, aryl, or aralkyl group having from 1–8 carbon atoms, $—OOCR^2$ or

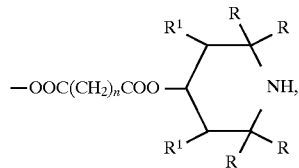

$R^2$ is $C_{1-8}$ alkyl, aryl or alkaryl group, and n is an integer from 2 to 10. Examples of the secondary amines include 2,2,6,6-tetramethylpiperidine (TMP), the acetic acid ester of 2,2,6,6-tetramethylpiperidin-4-ol (TMPOH), and bis (2,2,6,6-tetramethyl-4-piperidinyl) sebacate.

The electrophiles are preferably halides (bromides or iodides) or sulfonate esters:

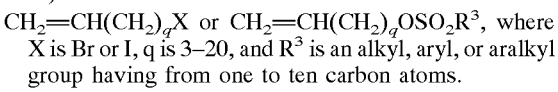
$CH_2=CH(CH_2)_qX$ or $CH_2=CH(CH_2)_qOSO_2R^3$, where X is Br or I, q is 3–20, and $R^3$ is an alkyl, aryl, or aralkyl group having from one to ten carbon atoms.

Electrophiles where X is Br or I may be formed in the reaction from the corresponding Cl or F substances by halide exchange with bromide or iodide salts. They are also formed by exchange of bromide or iodide salts with sulfonate electrophiles. While Example 8 below demonstrates the difficulty of using a chloride electrophile by itself, Examples 7, 9, and 11–15 show that an efficient bromide or iodide electrophile can be made in situ.

Cost, availability, solubility and vapor pressure are all factors which can affect the choice of leaving group present in the electrophile. The electrophilic compound preferably has a molecular weight less than about 600 and more than about 100. If added iodide anion is used (from an added iodide salt), it may be present in an amount between 0.005 mole equivalent and 1.2 mole equivalent (0.5 mole % to 120 mole %) of the electrophile.

The reaction is conducted with an excess of amine with respect to electrophile, i.e. at a molar ratio of amine to electrophile of from about 2 to about 10, and at a temperature between 100° C. and 200° C. At these ratios, the electrophile can be completely consumed. The solvent is as described below.

The two categories of solvent are N,N-dialkylamides and N,N,N',N'-tetraalkylureas:

$R^1R^2NCOR^7$ and $R^3R^4NCONR^5R^6$ where $R^{1-7}$ are independently chosen from alkyl, aryl, and alkaryl groups having from 1 to 12 carbon atoms; in addition, $R^7$ may be hydrogen, and any two R's may form a ring. An example of a ring compound is N-methylpyrrolidinone (NMP). Due to low cost, ready availability, low human toxicity and convenient physical properties, NMP is preferred. In NMP, $R^1$ and $R^7$ form a ring. It is also possible for $R^1$ and $R^2$ to form a ring. In the urea structure, rings can span $R^4$ and $R^5$, and they can connect $R^5$ and $R^6$.

Another way of expressing the suitable solvents is with the generic formula $(R^4)_2NCOR^8$ where $R^8$ is H, $C_{1-12}$ alkyl, aryl or alkaryl, or $N(R^4)_2$, each $R^4$ is independently selected from $C_{1-12}$ alkyl, aryl and alkaryl groups and any two R's may form a ring.

The choice of solvent may be based on high yield of the desired product, cost, ease of separation from products, ease of recycle, availability, human health effects, and other biological effects.

For convenience the reaction may be run at atmospheric pressure. Elevated or reduced pressures may be used, if desired. Low pressures are limited only by the vapor pressure of the components; since the reaction occurs in liquid, volatile components must have some concentration in the liquid phase.

Any hindered secondary amine which is recovered unreacted may be recycled.

Water is not beneficial in the system and is excluded by the use of dry solvents and reactants, and by blanketing the reaction mixture with an inert atmosphere. In the examples shown, solvent is separated from product and excess reactants by extraction of the NMP into water. This creates a disadvantage for the reuse of the solvent, since it must be dried beforehand. An alternative product isolation which maintains dry solvent is feasible. The ammonium salts present in the reaction mixture can be freed by a base which does not lead to coproduct water. Alkali metal alkoxides such as sodium methoxide can be used. Coproduct alcohol still needs to be removed, however.

DETAILED DESCRIPTION OF THE INVENTION

My invention is a method of making a hindered tertiary heterocyclic amine of the formula

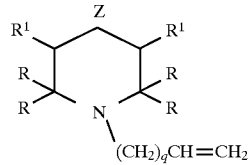

comprising reacting (a) a hindered heterocyclic amine of the formula

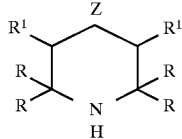

where each R is independently an alkyl group having from one to two carbon atoms, $R^1$ is H or $CH_3$, Z is a non-nucleophilic group, preferably H, an alkyl, aryl, or alkaryl group having from 1–8 carbon atoms, —$OOCR^2$ or

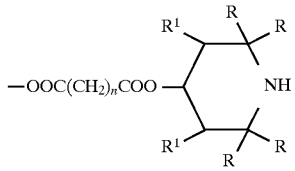

$R^2$ is $C_{1-8}$ alkyl, aryl or aralkyl, and n is 2 to 10, with (b) an electrophilic compound selected from bromides and iodides of the formula $CH_2$=$CH(CH_2)_qX$ where X is Br or I and q is 3–20, or $CH_2$=$CH(CH_2)_qOSO_2R^3$ where q is as above and $R^3$ is an alkyl, aryl, or aralkyl group having from one to ten carbon atoms, in the presence of a solvent of the formula $(R^4)_2NCOR^8$ where $R^8$ is H, $C_{1-12}$ alkyl, aryl or alkaryl or $N(R^4)_2$, each $R^4$ is independently selected from $C_{1-12}$ alkyl, aryl and alkaryl groups and any two R's may be connected in a ring, while maintaining the molar ratio of said tertiary ring amine to said electrophilic compound greater than 2, and recovering said heterocyclic hindered tertiary amine. It is understood that, in the above formulas the unspecified valences are occupied by hydrogen.

Suitable solvents include 1-ethyl-2-pyrrolidinone, 1-cyclohexyl-2-pyrrolidinone, 1-benzyl-2-pyrrolidinone, 1-butyl-2-pyrrolidinone, 1-octyl-2-pyrrolidinone, 1-(1,1,-dimethylethyl)-2-pyrrolidinone,1-hexyl-2-pyrrolidinone, 1-dodecyl-pyrrolidinone, 1-methyl-2-piperidinone, N-methylcaprolactam, N-formylmorpholine, N-formylpiperidine, 4-acetylmorpholine, N,N-dimethylformamide, N,N-diethylformamide, N,N-dimethylacetamide, N,N-diethylacetamide, 1,3-dimethyl-2-imidazolidinone (DMEU; N,N'-dimethylethyleneurea), 1,3-dimethyl-3,4,5,6-tetrahydro-2(1H)-pyrimidinone (DMPU; N,N'-dimethylpropyleneurea), 1-(2-ethylhexyl)-2-pyrrolidinone, tetramethylurea, tetraethylurea, N-methylformanilide, and tetrabutylurea.

A preferred form of the solvent has the formula

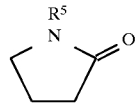

where $R^5$ is selected from alkyl, aryl, and aralkyl groups having from one to twelve carbon atoms. This includes the most preferred solvent, N-methylpyrrolidinone.

The invention is illustrated by the following examples.

EXAMPLE 1

Preparation of 1-(10-undecenyl)-2,2,6,6-tetramethylpiperidine.

Solvent N-methylpyrrolidinone (2459 g, $H_2O$<0.050) and TMP (1033 g, 98% by gas chromatography) were stirred and heated under inert atmosphere at atmospheric pressure. Granular potassium iodide (527 g) was added gradually over about 45 minutes. At a slurry temperature of 112° C., room temperature 11-bromo-1-undecene (647 g, 99% by gc) was added over five minutes. The slurry temperature at the beginning of the 11-bromo-1-undecene addition was 112° C. and 106° C. at the end. From 106° C., the temperature was raised to 120° C. within 15 minutes, maintained at 120°–135° C. for three hours and then 120°–100° C. for four hours. The slurry was cooled to 30° C. and partitioned between aqueous sodium hydroxide and hexane to give two homogeneous liquid layers. The upper organic layer was separated and distilled below atmospheric pressure at a maximum of 90° C. to remove a volatile mixture including hexane and TMP. Redistillation of the volatile mixture at atmospheric pressure gave recovered TMP suitable for reuse in alkylation. The portion remaining after hexane and TMP removal was short-path distilled at approximately 3 mm Hg. The portion boiling above 155° C. and below 164° C. was 704 g of clear liquid (98.9% by gc). It collected over 2.5 hours at a maximum pot temperature of 170° C. The desired structure was confirmed by NMR.

EXAMPLE 2

Attempted preparation of 4-hydroxy-1-(10-undecenyl-2,2,6, 6-tetramethylpiperidine using TMPOH.

A solution of N-methylpyrrolidinone (111 g) and TMPOH (55.7 g) was heated and stirred under inert atmosphere as granular potassium iodide (24.4 g) was added. When the slurry temperature was 90° C., 11-bromo-1-undecene (26.7 g) was added and the temperature was raised to 110° C. over twenty minutes, and then maintained at 110°–130° C. After one hour at 110°–130° C., an aliquot of the reaction mixture was cooled to room temperature and diluted with hexane. The hexane mixture was extracted once with excess aqueous sodium hydroxide and twice with water. Analysis of the hexane solution by gc showed the free hydroxyl result:

| component | retention time minutes | area % free hydroxyl | area % silyl. |
|---|---|---|---|
| undecadiene | 4.39 | 5.3 | 3.4 |
| 1-iodo-10-undecene | 18.17 | 7.1 | 5.0 |
| O-undecylated TMPOH | 24.36 | 3.3 | 2.5 |
| N-undecylated TMPOH | 26.21 | 77.7 | — |
| N-undecylated TMPOSi (CH$_3$)$_3$ | 26.22 | — | 81.6 |
| N,O-diundecylated TMPOH | 34.03 | 1.5 | 1.0 |

For the silylated analysis, the hexane solution was silylated in the presence of acetone and excess N,O-bis(trimethylsilyl)acetamide. As can be seen in the results above, the undesired O-undecenylated byproduct was formed.

EXAMPLE 3

Preparation of 4-hydroxy-1-(10-undecenyl)-2,2,6,6-tetramethylpiperidine using bis(2,2,6,6-tetramethyl-4-piperidinyl) sebacate.

Part 1. Alkylation.

Solvent N-methylpyrrolidinone (629 g, H$_2$O<0.05%), bis(2,2,6,6-tetramethyl-4-piperidinyl) sebacate (500.5 g) and 11-bromo-1-undecene (140.1 g, 98.3% by gc) were heated and stirred under inert atmosphere. Beginning at 100° C., granular potassium iodide (95.5 g) was gradually added over one hour, with a slurry temperature of 138° C. at the end of the hour. The slurry was stirred at 135°–140° C. for an additional eighteen hours, then cooled to room temperature. The slurry was diluted with heptane and methyl butyrate, and ammonium salts were freed by adding 60 g 50% aqueous sodium hydroxide and 400 mL water. After mixing, two clear liquid layers separated. The aqueous layer was extracted with heptane and the combined organic portions were extracted four times with water. The organic layer was concentrated on a rotary evaporator, then heated at about 3 mm Hg. The clear brown liquid remaining was 588.5 g.

Part 2. Hydrolysis.

The crude product from part 1 was stirred and heated to reflux for 58 hours with potassium hydroxide pellets (280 g) and water (1.5 L). The mixture was cooled in an ice bath without agitation. The aqueous layer containing dissolved potassium sebacate was drained off. The waxy organic was triturated with hexane (4×300 mL) and all the hexane portions were passed through a fritted glass filter. The solid retained in the filter was TMPOH and weighed 180 g after drying. The filtrate was concentrated on a rotary evaporator to 177.5 g dark brown oil.

Part 3. Distillation.

Short-path distillation at about 3 mm Hg gave a small forecut of TMPOH, followed by 4-hydroxy-1-(10-undecenyl)-2,2,6,6-tetramethylpiperidine (152.6 g) at 185°–188° C. head temperature and 190°–200° C. pot temperature. The distillate was collected with an air-cooled condenser. It set to a waxy solid after briefly chilling the hot distillate with dry ice. The distillate remained solid at room temperature. It was heated, melted and then swirled to homogenize. An aliquot was diluted in acetone for analysis by gc: 0.2% TMPOH by area at 5.31 minute retention time, and 99.2% product at 26.05 minute retention time. No O-alkylated byproduct was found, while the smallest impurity detected was 0.02% by area at 25.03 minute retention time. The structure was confirmed by NMR; the terminal unsaturated group was present.

Persons skilled in the art will recognize that at the end of the Alkylation step, a mixture was obtained which contained mono-N-undecenyl and di-N-undecenyl derivatives of bis(2,2,6,6-tetramethyl-4-piperidinyl) sebacate as well as starting material. Hydrolysis converted this mixture to TMPOH and 4-hydroxy-1-(10-undecenyl)-2,2,6,6-tetramethylpiperidine.

No ether impurities were detected in Example 3 in contrast to Example 2, where they were present. Persons skilled in the art will observe that my method provides high yields of tertiary amines in reduced reaction times. The products can be isolated in a high state of purity without difficult and expensive chromatography or recrystallization. In some cases extraction followed by simple vacuum distillation gives pure product. Sensitive electrophiles such as terminal alkenes may react selectively without isomerization to internal alkenes. The side reaction of oxygen alkylation during attempted N-alkylation of hindered aminoalcohols may be totally averted by the use of ester protecting groups. The esters are easily removed after N-alkylation by nucleophiles. Suitable nucleophiles include water, alkali hydroxides and alkali alkoxides.

EXAMPLE 4

Preparation of 1-(4-pentenyl)-2,2,6,6-tetramethylpiperidine using a sulfonate ester.

Solvent N-methylpyrrolidinone (456 g, water<0.05%) and TMP (363.9 g, 98.1% by gc) were heated and stirred under inert atmosphere. At 120° C. solution temperature the methanesulfonate ester of 4-penten-1-ol (164.9 g, 99.8% by gc) was added and the temperature was maintained at 110°–130° C. Potassium iodide (8.4 g) was added ninety minutes after the sulfonate ester. Twenty hours after the sulfonate ester addition the mixture was cooled to 95° C. and water (200 mL) was added. Aqueous sodium hydroxide (82.6 g) was added to the room temperature mixture, and the aqueous and organic layers were separated. The aqueous layer was extracted twice with hexane and the combined organic portions were extracted three times with water. The organic portion was concentrated on a rotary evaporator then short-path distilled at about 3 mm Hg. The distillate at 80°–87° C. head temperature and 88° C. pot temperature was 1-(4-pentenyl)-2,2,6,6-tetramethylpiperidine (133.6 g), a clear colorless liquid. Analysis by gc showed 95.5% by area product.

EXAMPLE 5

Preparation of 1-(4-pentenyl)-2,2,6,6-tetramethylpiperidine using 1-iodo-4-pentene. Solvent N-methylpyrrolidinone (499 g, water<0.05%) and TMP (397.0 g, 99.4% by gc) were heated and stirred under inert atmosphere. Neat room temperature 1-iodo-4-pentene (212.8 g, 99.0 % by gc) was added in one portion to the 120° C. reaction mixture, giving a temperature of 112° C. Within ten minutes the solution temperature was 126° C., and a temperature of 120°–140° C. was maintained for fourteen hours. The mixture was cooled to 45° C. and aqueous sodium hydroxide (91 g 50% aqueous sodium hydroxide diluted with water to 400 mL total volume) was introduced. At 28° C. hexane (200 mL) was added and the layers were separated. The aqueous layer was extracted with hexane (2×400 mL) and the combined organic portions were extracted with water (4×60 mL). Concentration on a rotary evaporator at reduced pressure and 95° C. bath temperature left 269.6 g of clear orange liquid. Short-path distillation at about 15 mm Hg, 107°–114° C. head temperature and 112°–120° C. pot temperature gave 1-(4-pentenyl)-2,2,6,6-tetramethylpiperidine (183.6 g) as a clear colorless liquid. An aliquot diluted in methanol was analyzed by gc as 0.2 area % TMP and 99.2% product. The product structure was confirmed by NMR; only the terminal olefin was present.

EXAMPLE 6

Preparation of 1-(5-hexenyl)-2,2,6,6-tetramethylpiperidine using a sulfonate ester in the absence of added iodide.

A mixture of TMP (407.8 g, 99.4% by gc) and 5-hexenyl methanesulfonate (152.2 g, 96.60% by gc) was heated and stirred at atmospheric pressure under argon in N-methylpyrrolidinone (550 g, $H_2O$<0.05%). After twelve hours at 145°±15° C., the mixture was cooled. At 90° it set to a solid and water (200 mL) was added to give a stirred solution. Aqueous sodium hydroxide (110 g, 50% by weight) was added and the stirred mixture was cooled to room temperature. Water (300 mL) and hexane (300 mL) were added and the layers were separated. The lower aqueous layer was extracted with hexane (3×100 mL). The combined organic layers were extracted with water (4×75 mL). The organic layer was concentrated on a rotary evaporator at 85° C. and 60 mm Hg to 213.0 g black liquid. Short-path distillation at 14 mm Hg removed a forecut up to 129° head temperature at 136° pot temperature. The product (99.8 g) distilled at 130°–135° head temperature and 137°–145° pot temperature. The main cut was a pale yellow liquid, 97.1% pure by gc area.

EXAMPLE 7

Preparation of 1-(10-undecenyl)-2,2,6,6-tetramethylpiperidine in 1,1,3,3-tetramethylurea.

A mixture of 1,1,3,3-tetramethylurea (816.7 g, $H_2O$<0.01%), TMP (381.7 g, >99% by gc) and potassium iodide (149.0 g, 0.898 mole) was stirred under argon at 125° C. Neat 11-chloro-1-undecene (170.9 g) was added and the mixture was stirred at 120°–130° C. for twenty-four hours. The mixture was brought to 20° C. with stirring and then poured into a separatory funnel using hexane (300 mL) and water (600 mL) containing aqueous sodium hydroxide (98 g of 50% by weight). The mixture was shaken and the layers were separated. The lower aqueous layer (1.5 L) was extracted with hexane (3×500 mL). The organic portions were combined and extracted with water (2×50 mL). The organic portion was concentrated on a rotary evaporator at 95° C. bath temperature and reduced pressure to a clear brown liquid (350.8 g). Short-path distillation at about 3 mm Hg removed a forecut up to 134° C. head temperature at 156° C. pot temperature. The main cut (229.9 g) was a clear yellow liquid. Assay by gc was 98%. The pot residue (4.2 g) was a brown tar.

EXAMPLE 8

Attempted Preparation of 1-(10-undecenyl-2,2,6,6-tetramethylpiperidine using 11-chloro-1-undecene.

A mixture of N,N-dimethylpropionamide (198 g), TMP (100.3 g) and 11-chloro-1-undecene (43.6 g) was stirred under argon and heated to reflux (162°–169° C). After one day at reflux an aliquot was partitioned between hexanes and aqueous sodium hydroxide and analyzed by gc: the 11-chloro-1-undecene was largely unchanged. After seven days reflux, similar analysis showed consumption of about half the 11-chloro-1-undecene. After eight days reflux the mixture was cooled to room temperature and partitioned between 50% aqueous sodium hydroxide (24 g) hexanes (250 mL) and sufficient water to dissolve all the salts. The organic layer was separated and the lower layers of water and solvent were extracted with hexanes (4×100 mL). The organic portions were combined and extracted with water (1×30 mL). The organic layer was concentrated on a rotary evaporator at about 60 mm Hg and 95° C. bath temperature to a brown oil (64.5 g). Short-path distillation at about 3 mm Hg gave a forecut (7.6 g) with maximum boiling point 107° C. Continued distillation at 150°–160° C. gave a main cut (42.1 g) which was 83.6% pure by gc.

This example demonstrates slow reaction when the halogen of the electrophile is chlorine rather than bromine or iodine. This leads to incomplete electrophile conversion and low yield, even with prolonged heating.

EXAMPLE 9

Preparation of 1-(10-undecenyl)-2,2,6,6-tetramethylpiperidine using 11-iodo-1-undecene.

A mixture of TMP (391 g), N,N-dimethylacetamide (802.0 g, $H_2O$<0.01%), 11-chloro-1-undecene (175.5 g) and potassium iodide (141.2 g) was stirred and heated under argon. After twenty-one hours at 120°–130° C., the mixture was cooled to room temperature. It was partitioned between hexanes and aqueous sodium hydroxide (105 g of 50% by weight) with sufficient added water to dissolve all salts. The lower aqueous layer (1.75 L) was drained from the upper organic layer (1.2 L) and the aqueous layer was extracted with hexanes (4×200 mL). The combined organic portions were extracted with water (2×50 ml) and concentrated on a rotary evaporator at about 60 mm Hg and 95° C. bath temperature to an amber liquid (345 g). Short-path distillation at 3 mm Hg and 120°–140° C. gave clear liquid (242.6 g, 98.5% pure by gc).

This example shows that halide exchange during the reaction may convert the ineffective 11-chloro-1-undecene into 11-iodo-1-undecene.

EXAMPLE 10

Preparation of 1-(10-undecenyl)-2,2,6,6-tetramethylpiperidine using 11-bromo-1-undecene.

A mixture of TMP (102.2 g), anhydrous lithium bromide (18.6 g), 11-chloro-1-undecene (43.1. g, 99.3 by gc) and 1,3-dimethyl-2-imidazolidinone (199.4 g, $H_2O$<0.1%) was stirred under argon. After fifty-five hours at 120°–140° C., the mixture was cooled to room temperature and partitioned between hexanes (150 mL), aqueous sodium hydroxide (25 g of 50% by weight) and sufficient water to dissolve all salts. The upper organic layer (350 mL) was separated and the aqueous layer (400 mL) was extracted with hexanes (4×100 mL). The organic portions were combined and extracted with water (2×30 mL). The organic layer was concentrated on a rotary evaporator at about 60 mm Hg in a water bath at 95° C. to a clear liquid (75.5 g). Short-path distillation at about 3 mm Hg and about 145° C. head temperature gave a colorless liquid (43.6 g, 95.1% purity by gc).

This example shows that halide exchange during the reaction may convert the ineffective 11-chloro-1-undecene into 11-bromo-1-undecene.

EXAMPLE 11

Preparation of 1-(10-undecenyl)-2,2,6,6-tetramethylpiperidine in 1,3-dimethyl-2-imidazolidinone.

A mixture of TMP (386 g), 11-chloro-1-undecene (176 g), potassium iodide (147.5 g) and 1,3-dimethyl-2-imidazolidinone (802 g) was stirred and heated under argon. After nine hours at 120°–140° C., the mixture was cooled to room temperature and partitioned between 50% aqueous sodium hydroxide (101 g), hexanes (500 mL) and sufficient water to dissolve all the salts. The upper organic layer (1 L) was separated and the lower aqueous layer was extracted with hexanes (3×200 mL). The organic portions were combined and extracted with water (2×50 mL). The organic layer was concentrated on a rotary evaporator to an amber liquid (346 g). Short-path distillation at about 1 mm Hg and 107°–154° C. head temperature gave a hazy liquid (239.9 g, 93.9% pure by gc).

EXAMPLE 12

Preparation of 1-(10-undecenyl)-2,2,6,6-tetramethylpiperidine in N-formylmorpholine.

A mixture of TMP (387 g), 11-chloro-1-undecene (173 g), potassium iodide (150 g) and N-formylmorpholine (804 g) was stirred and heated under argon. After twenty hours at 105°–125° C., the mixture was cooled to room temperature and partitioned between 50% aqueous sodium hydroxide (101 g), hexanes (500 mL) and sufficient water to dissolve most of the solids. The upper organic layer (1 L) was separated and the lower aqueous layer (1.7 L) was extracted with hexanes (3×300 mL). The organic portions were combined and extracted with water (2×100 mL). The organic layer was concentrated on a rotary evaporator to an amber liquid (328 g). Short-path distillation at about 1 mm Hg and 107°–122° C. head temperature gave a clear liquid (234.4 g, 97.2% pure by gc).

EXAMPLE 13

Preparation of 1-(10-undecenyl)-2,2,6,6-tetramethylpiperidine in N,N-dimethylformamide.

A mixture of TMP (387 g), 11-chloro-1-undecene (177 g), potassium iodide (145 g) and N,N-dimethylformamide (805 g) was stirred and heated under argon. After twenty-three hours at 120°–130° C., the mixture was cooled to room temperature and partitioned between 50% aqueous sodium hydroxide (128 g), hexanes (500 mL) and sufficient water to dissolve all of the solid. The upper organic layer (1 L) was separated and the lower aqueous layer (1.7 L) was extracted with hexanes (3×200 mL). The organic portions were combined and extracted with water (1×50 mL). The organic layer was concentrated on a rotary evaporator at 95° C. bath temperature and about 60 mm Hg to a brown liquid (343 g). Short-path distillation at about 1 mm Hg and 111°–141° C. head temperature gave a clear liquid (236.6 g, 97.9% pure by gc).

EXAMPLE 14

Preparation of 1-(10-undecenyl)-2,2,6,6-tetramethylpiperidine in N-methylpyrrolidinone (NMP).

A mixture of TMP (387 g), 11-chloro-1-undecene (175 g), potassium iodide (143 g) and NMP (802 g) was stirred and heated under argon. After nineteen hours at 120°–130° C., the mixture was cooled to room temperature and partitioned between 50% aqueous sodium hydroxide (100 g) hexanes (500 mL) and sufficient water to dissolve all of the salts. The upper organic layer (1 L) was separated and the lower aqueous layer (1.7 L) was extracted with hexanes (3×200 mL). The organic portions were combined and extracted with water (2×50 mL). The organic layer was concentrated on a rotary evaporator to a brown liquid (368 g). Short-path distillation at about 3 mm Hg and 120°–152° C. head temperature gave a clear liquid (243.5 g 98.9% pure by gc).

EXAMPLE 15

Preparation of 1-(10-undecenyl)-2,2,6,6-tetramethylpiperidine in N-cyclohexylpyrrolidinone.

A mixture of TMP (385 g), 11-chloro-1-undecene (173 g), potassium iodide (143 g) and N-cyclohexylpyrrolidinone (801 g) was stirred and heated under argon. After twenty-one hours at 120°–130° C., the mixture was cooled to room temperature and partitioned between aqueous sodium hydroxide and hexanes (400 mL) to give three liquid layers. The top brown hexanes layer (800 mL) was separated and the bottom clear colorless aqueous salt layer (250 mL) was drained off. The middle dark brown layer of aqueous N-cyclohexylpyrrolidinone (1400 mL) was extracted with hexanes (3×200 mL). The hexanes portions were combined and extracted with water (3×50 mL) then concentrated on a rotary evaporator to a clear red liquid (407 g). Short-path distillation at about 1 mm Hg gave a fraction boiling at head temperature above 100° C. (230.9 g, 98.0% pure by gc).

EXAMPLE 16

Preparation of 1-(10-undecenyl)-2,2,6,6-tetramethylpiperidine using 11-bromo-1-undecene.

A mixture of TMP (63.8 g), 11-bromo-1-undecene (35.2 g) and N-methylpyrrolidinone (130 g) was stirred and heated under argon. After sixteen hours at 160°–170° C., the mixture was cooled to room temperature and partitioned between hexanes (250 mL) and 50% aqueous sodium hydroxide (15.7 g). Sufficient water was added to dissolve all salts. The upper clear brown hexanes layer (300 mL) was separated and the lower hazy brown aqueous layer (225 mL) was extracted with hexanes (3×80 mL). The combined hexanes portions were extracted with water (1×25 mL) then concentrated on a rotary evaporator to a brown liquid (60.3 g). Short-path distillation at about 3 mm Hg gave a fraction boiling at head temperature 130°–160° C. (35.6 g, 98.4% pure by gc).

EXAMPLE 17

Preparation of 1-(10-undecenyl)-2,2,6,6-tetramethylpiperidine using 11-bromo-1-undecene at lower temperatures.

The procedure of Example 16 was repeated at 120°–130° C. for twenty-four hours. The distillate obtained at about 3 mm Hg and 158°–165° C. head temperature was a clear liquid (35.5 g, 98.1% pure by gc).

EXAMPLE 18

Preparation of 1-(10-undecenyl)-2,2,6,6-tetramethylpiperidine using 11-bromo-1-undecene in N-methylcaprolactam.

The procedure of Example 17 was repeated, using N-methylcaprolactam solvent for twenty-six hours at 120°–130° C. Distillation at about 3 mm Hg and 132°–165° C. head temperature gave a clear liquid (33.6 g, 94.70% pure by gc).

EXAMPLE 19

Preparation of 1-(10-undecenyl)-2,2,6,6-tetramethylpiperidine using 11-bromo-1-undecene without solvent.

A mixture of TMP (195 g) and 11-bromo-1-undecene (105.5 g) was heated and stirred under argon. After sixty-five hours at 160°–175° C. the mixture was cooled to room temperature and partitioned between 50% aqueous sodium hydroxide (39.6 g), hexanes (250 mL) and sufficient water to dissolve all salts. The lower clear colorless aqueous layer (140 mL) was removed. The upper organic layer (500 mL) was extracted with water (2×25 mL) and concentrated on a rotary evaporator at about 60 mm Hg in a 90° C. water bath to a clear orange liquid (174.7 g). Short-path distillation at about 3 mm Hg gave a clear liquid fraction boiling at 130°–161° C. (82.2 g, 96.5% pure by gc).

This example shows that yield is reduced and reaction time is prolonged without solvent.

The compounds made by my process are useful as precursors of light stabilizers in plastics.

I claim:
1. Method of making a heterocyclic hindered tertiary amine of the formula

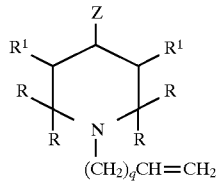

comprising reacting (a) a hindered heterocyclic amine of the formula

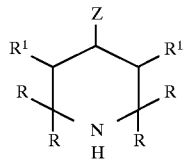

where each R is independently an alkyl group having from one to two carbon atoms, each $R^1$ is H or $CH_3$, and Z is H, an alkyl, aryl, or alkaryl group having from 1–8 carbon atoms, $—OOCR^2$ or

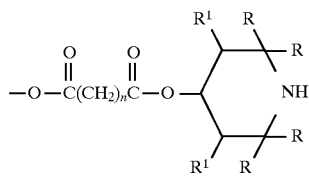

$R^2$ is $C_{1-8}$ alkyl, aryl or aralkyl, and n is an integer from 2 to 10, with (b) an electrophilic compound selected from halides of the formula $CH_2=CH(CH_2)_qX$ where X is Br or I and q is 3–20 or an electrophilic compound of the formula $CH_2=CH(CH_2)_qOSO_2R^3$ where q is as above and $R^3$ is an alkyl, aryl, or aralkyl group having from one to ten carbon atoms, in the presence of a solvent of the formula $(R^4)_2NCOR^8$ where $R^8$ is H, $C_{1-12}$ alkyl, aryl or alkaryl or $N(R^4)_2$, each $R^1$ is independently selected from $C_{1-12}$ alkyl, aryl and alkaryl groups and any two R's may be connected in a ring, while maintaining the molar ratio of said heterocyclic amine to said electrophilic compound greater than 2, and recovering said heterocyclic hindered tertiary amine.

2. Method of claim 1 wherein Z is

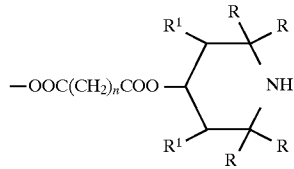

where n is an integer from 2 to 10.

3. Method of claim 1 wherein Z is $—OOCR^2$ and $R^2$ is an alkyl group having from 1–8 carbon atoms.

4. Method of claim 1 wherein Z is an alkyl group having from 1–8 carbon atoms.

5. Method of claim 1 wherein said hindered heterocyclic amine is a 2,2,6,6-tetraalkyl piperidine and said hindered tertiary amine is a 1-substituted 2,2,6,6-tetraalkyl piperidine.

6. Method of claim 5 wherein said heterocyclic hindered amine is 2,2,6,6-tetramethylpiperidine.

7. Method of claim 1 wherein said solvent has the formula:

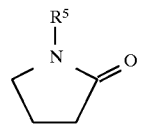

where $R^5$ is selected from alkyl, aryl, and aralkyl groups having from one to twelve carbon atoms.

8. Method of claim 7 wherein said solvent is N-methylpyrrolidinone.

9. Method of claim 1 wherein said electrophilic compound has a molecular weight less than about 600 and the reaction is conducted at a temperature between about 100° C. and about 200° C.

10. Method of claim 1 wherein said electrophilic compound has a molecular weight more than 100 and the reaction is conducted at a temperature between about 100 and about 200° C.

11. Method of claim 3 wherein said heterocyclic amine is the acetic acid ester of 4-hydroxy-2,2,6,6-tetramethylpiperidine.

12. Method of claim 2 wherein said hindered heterocyclic amine is the diester of 4-hydroxy-2,2,6,6-tetramethylpiperidine and sebacic acid.

13. Method of claim 1 wherein an iodide salt is present in the reaction in an amount of 0.5% to 120% molar equivalent of the electrophile.

14. Method of claim 1 wherein hindered heterocyclic amine reactant (a) is the benzoic acid ester of 4-hydroxy-2, 2,6,6-tetramethylpiperidine.

15. Method of claim 1 wherein the molar ratio of amine to electrophile is from about 2 to about 10.

16. Method of claim 1 from which water is excluded.

17. Method of claim 1 wherein the electrophile is made in situ from a compound of the formula $CH_2=CH(CH_2)_qCl$ q is an integer from 3–20.

18. Method of making a heterocyclic hindered tertiary amine of the formula

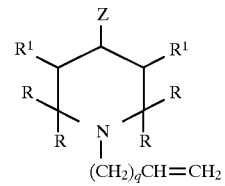

comprising reacting (a) a hindered heterocyclic amine of the formula

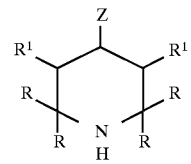

where each R is independently an alkyl group having from one to two carbon atoms, each $R^1$ is H or $CH_3$, and Z is a non-nucleophilic group, with (b) an electrophilic compound selected from halides of the formula $CH_2=CH(CH_2)_qX$ where X is Br or I and q is 3–20 or an electrophilic compound of the formula $CH_2=CH(CH_2)_qOSO_2R^3$ where q is as above and $R^3$ is an alkyl, aryl, or aralkyl group having from one to ten carbon atoms, in the presence of a solvent of the formula $(R^4)_2NCOR^8$ where $R^8$ is H, $C_{1-12}$ alkyl, aryl or alkaryl or $N(R^4)_2$, each $R^4$ is independently selected from $C_{1-12}$ alkyl, aryl and alkaryl groups and any two R's may be connected in a ring, while maintaining the molar ratio of said heterocyclic amine to said electrophilic compound greater than 2, and recovering said heterocyclic hindered tertiary amine.

19. Method of making 1-(10-undecenyl)-2,2,6,6-tetramethylpiperidine comprising reacting 2,2,6,6-tetramethylpiperidine with 11-bromo-1-undecene in a solvent of N-methylpyrrolidinone.

20. Method of making a compound of the formula

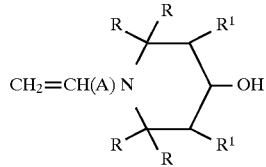

comprising reacting a compound of the formula

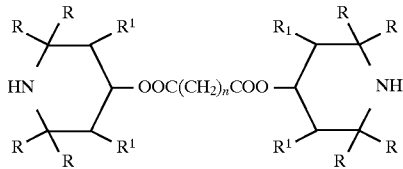

with a compound of the formula $CH_2$=$CH(A)X$ or $CH_2$=$CH(A)OSO_2R^3$ in the presence of a solvent of the formula $(R^4)_2NCOR^8$ where $R^8$ is H, $C_{1-12}$ alkyl, aryl or alkaryl or $N(R^4)_2$, each $R^4$ is independently selected from $C_{1-12}$ alkyl, aryl and alkaryl groups and any two R's may be connected in a ring, and hydrolyzing the reaction product, wherein (A) is $(CH_2)_{3-20}$, n is an integer from 2 to 10, X is Br or I, and $R^3$ is an alkyl, aryl, or alkaryl group having from one to twenty carbon atoms.

21. Method of claim 20 wherein n is 8.
22. Method of claim 20 wherein (A) is $(CH_2)_9$.
23. Method of claim 20 wherein (A) is $(CH_2)_9$ and n is 8.
24. Method of claim 20 wherein an iodide salt is also present.

* * * * *